United States Patent
Bohlen

(10) Patent No.: US 7,316,736 B2
(45) Date of Patent: Jan. 8, 2008

(54) CARBON FILTER PANEL FOR AN AIR CLEANER

(75) Inventor: John R. Bohlen, Biloxi, MS (US)

(73) Assignee: Oreck Holdings LLC, Cheyenne, WY (US)

( * ) Notice: Subject to any disclaimer, the term of this patent is extended or adjusted under 35 U.S.C. 154(b) by 332 days.

(21) Appl. No.: 11/148,056

(22) Filed: Jun. 8, 2005

(65) Prior Publication Data

US 2006/0277876 A1    Dec. 14, 2006

(51) Int. Cl.
*B01D 53/04* (2006.01)
*F24F 3/16* (2006.01)

(52) U.S. Cl. .............................. 96/131; 96/147; 55/484; 55/497

(58) Field of Classification Search .................. 96/108, 96/121, 131, 147, 154; 55/482, 484, 490, 55/495, 497, 511, 529
See application file for complete search history.

(56) References Cited

U.S. PATENT DOCUMENTS

| | | | |
|---|---|---|---|
| 2,303,332 A | | 12/1942 | Dauphinee |
| 3,853,519 A | * | 12/1974 | York, Jr. .................... 96/129 |
| 4,244,710 A | | 1/1981 | Burger |
| 4,518,704 A | | 5/1985 | Okabayashi et al. |
| 4,699,681 A | * | 10/1987 | Kasmark et al. ............ 156/264 |
| 5,354,365 A | * | 10/1994 | Youn .......................... 96/135 |
| 5,593,481 A | | 1/1997 | Redner et al. |
| 5,730,918 A | | 3/1998 | Nikolskaja et al. |
| 6,171,373 B1 | | 1/2001 | Park et al. |
| 6,352,578 B1 | * | 3/2002 | Sakata et al. ................ 96/134 |
| 6,372,289 B1 | | 4/2002 | Hickman |
| 6,413,303 B2 | | 7/2002 | Gelderland et al. |
| 6,787,494 B2 | | 9/2004 | Tsuji et al. |
| 2002/0155252 A1 | | 10/2002 | Tsuji et al. |

FOREIGN PATENT DOCUMENTS

IT    MI930772 U1    4/1995

* cited by examiner

*Primary Examiner*—Frank M. Lawrence
(74) *Attorney, Agent, or Firm*—The Ollila Law Group LLC

(57) ABSTRACT

A carbon filter panel for an air cleaner is provided according to an embodiment of the invention. The carbon filter panel includes a frame including one or more side members and a frame interior space and a plurality of spaced-apart carbon elements extending across the frame interior space. Airflow can pass between the plurality of carbon elements and through the carbon filter panel.

26 Claims, 7 Drawing Sheets

CARBON FILTER PANEL FOR AN AIR CLEANER

TECHNICAL FIELD

The present invention relates to filter panel for an air cleaner, and more particularly, to carbon filter panel for an air cleaner.

BACKGROUND OF THE INVENTION

Air cleaners and purifiers are widely used for removing foreign substances from the air. An air cleaner can be used in many settings, including at home, in offices, workrooms, etc. The foreign substances can include pollen, dander, smoke, pollutants, dust, etc. In addition, an air cleaner can be used to remove odors from the air.

One type of filter for use in an air cleaner is a carbon filter. A carbon filter can remove various contaminant particles and resulting odors from the air. Some odors desired to be removed in a residential setting are smoke, kitchen or food odors, pet odors, body odors, automobile exhaust, and cleaning compounds, to name a few. In addition, activated carbon can further remove various organic gases, radon, and ozone, among others.

Activated carbon air filters comprise a carbon material that includes a large number of molecular pores. These pores are highly adsorbent, forming a strong chemical bond/attraction to odorous, gaseous, and liquid contaminates. Activated carbon is essentially charcoal that has been treated with oxygen in order to open up millions of tiny pores between the carbon atoms, resulting in a highly adsorbent material.

In the prior art, a carbon filter typically comprises a mesh or layer of fibers that are coated with carbon particles or granules. The carbon particles are typically held to the mesh or fibers by some manner of bonding agent. One typical bonding agent is a resin.

However, this prior art approach has drawbacks. The bonding agent typically is not completely covered by carbon. In addition, the carbon bonded to the mesh or fibers is typically relatively thin. As a result, such a prior art carbon filter is quickly used up and loses odor adsorption capability in an undesirably short time.

SUMMARY OF THE INVENTION

A carbon filter panel for an air cleaner is provided according to an embodiment of the invention. The carbon filter panel comprises a frame including one or more side members and a frame interior space and a plurality of spaced-apart carbon elements extending across the frame interior space. Airflow can pass between the plurality of carbon elements and through the carbon filter panel.

A carbon filter panel for an air cleaner is provided according to an embodiment of the invention. The carbon filter panel comprises a frame including one or more side members and a frame interior space and a plurality of apertures formed in the frame and opening into at least the frame interior space. The carbon filter panel further comprises a plurality of spaced-apart carbon elements extending across the frame interior space. Ends of the plurality of carbon elements are received in the plurality of apertures. Airflow can pass between the plurality of carbon elements and through the carbon filter panel.

A carbon filter panel for an air cleaner is provided according to an embodiment of the invention. The carbon filter panel comprises a frame including one or more side members and a frame interior space and a plurality of apertures formed in the frame and opening into at least the frame interior space. The plurality of apertures are formed in two or more aperture rows. The carbon filter panel further comprises a plurality of spaced-apart carbon elements extending across the frame interior space in two or more carbon element rows. Ends of the plurality of carbon elements are received in the plurality of apertures. Airflow can pass between the plurality of carbon elements and through the carbon filter panel.

A carbon filter panel for an air cleaner is provided according to an embodiment of the invention. The carbon filter panel comprises a frame including one or more side members and a frame interior space and a plurality of apertures formed in the frame and opening into at least the frame interior space. The plurality of apertures are formed in two or more aperture rows. The carbon filter panel further comprises a plurality of spaced-apart carbon elements extending across the frame interior space in two or more non-aligned carbon element rows. Ends of the plurality of carbon elements are received in the plurality of apertures. Airflow can pass between the plurality of carbon elements and through the carbon filter panel.

BRIEF DESCRIPTION OF THE DRAWINGS

The same reference number represents the same element on all drawings. It should be noted that the drawings are not necessarily to scale.

DETAILED DESCRIPTION OF THE INVENTION

FIGS. 1-8 and the following descriptions depict specific embodiments to teach those skilled in the art how to make and use the best mode of the invention. For the purpose of teaching inventive principles, some conventional aspects have been simplified or omitted. Those skilled in the art will appreciate variations from these embodiments that fall within the scope of the invention. Those skilled in the art will also appreciate that the features described below can be combined in various ways to form multiple variations of the invention. As a result, the invention is not limited to the specific embodiments described below, but only by the claims and their equivalents.

Figure 1:
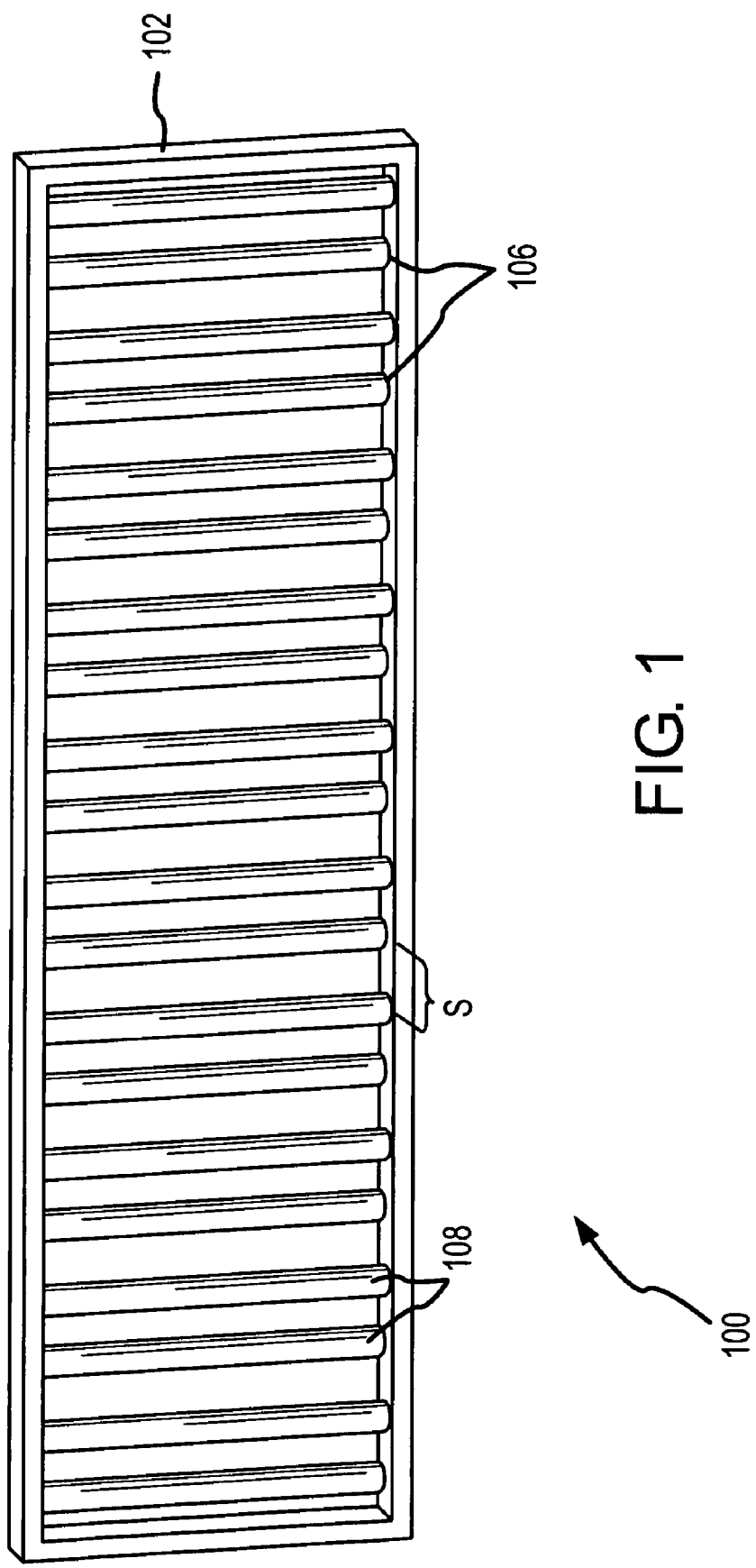
FIG. 1 shows a carbon filter panel according to an embodiment of the invention.

FIG. 1 shows a carbon filter panel 100 according to an embodiment of the invention. The carbon filter panel 100 in this embodiment comprises a frame 102, a plurality of apertures 106 formed in substantially opposite sides of the frame 102, and a plurality of spaced-apart carbon elements 108 extending between the substantially opposite sides of the frame 102. The carbon elements 108 are received in the apertures 106. The carbon elements 108 are spaced-apart by a separation distance S. The carbon elements 108 can be regularly spaced, wherein each carbon element 108 is the distance S from another carbon element 108. Alternatively, the carbon elements 108 can be separated by random or varying separation distances.

The apertures 106 in one embodiment comprise blind apertures in the frame 102. Alternatively, the apertures 106 can pass through the frame 102, wherein each carbon element 108 includes a smaller end portion 305 (see also FIG. 3) that is received in an aperture 106.

The shape of the frame 102 can be designed for a particular application. In the embodiment shown, the frame 102 is substantially rectangular. However, it should be understood that the frame 102 can comprise any shape, including for example, square, round, oval, or even multi-sided.

The frame 102 can include one or more side members. In the embodiment shown, the frame 102 includes four side members in order to form a substantially rectangular frame 102. The frame 102 can be of any desired size. Therefore, the carbon elements 108 can be of any needed length. Similarly, the frame can be formed of any desired material. In one embodiment, the frame 102 is also formed substantially of carbon, wherein the entire carbon filter panel 100 is formed substantially of carbon. Alternatively, the frame 102 can be formed partially of carbon or can be formed entirely of other materials.

The carbon elements 108 can be formed in one or more rows in the frame 102. For a single row, the carbon elements 108 can be held in a substantially straight line by the frame 102. The figure shows two rows of carbon elements 108 that are formed on two separate lines A and B (see also FIGS. 4 and 5). If the frame 102 is sufficiently wider than the carbon elements 108, then the rows can be fully offset, wherein the individual carbon elements 108 of a first row do not overlap the individual carbon elements 108 of a second row.

A carbon element 108 can be formed in any manner. The carbon element 108 can be formed of carbon particles or granules mixed with a binder of any manner. The carbon element 108 can be extruded, molded, machined, cut, etc. In addition, heat can be used to cure the binder and/or to fuse the carbon material. The heat can include a sintering process, wherein a coherent shape is formed by heating without melting a carbon powder in order to form a carbon element 108.

In one embodiment, the carbon elements 108 can be ground, sanded, ablated, turned, or otherwise reduced in size. This reduction allows a small outer layer to be removed when a carbon element 108 is at or near saturation with contaminants. Consequently, the adsorption capacity of a carbon element 108 can be substantially renewed.

Figure 2C:
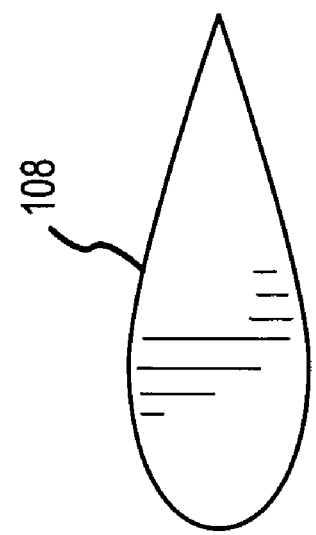
FIGS. 2A-2C show several possible cross-sectional shapes of the carbon element.
Figure 2B:
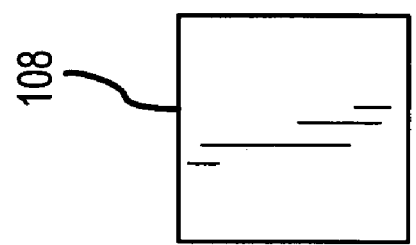
Figure 2A:
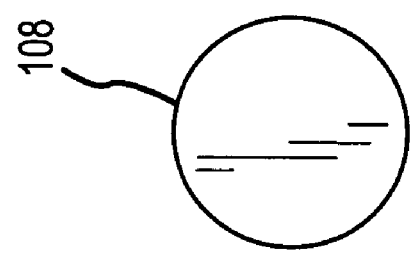

FIGS. 2A-2C show several possible cross-sectional shapes of the carbon element 108. In FIG. 2A, the carbon element 108 comprises a substantially cylindrical cross-section, such as a cylindrical rod. In FIG. 2B, the carbon element 108 comprises a substantially rectangular cross-section, such as a rectangular bar. In FIG. 2C, the carbon element 108 comprises an airfoil cross-section, wherein airflow resistance is reduced and turbulence downstream of the carbon element 108 is minimized. However, it should be understood that the carbon element 108 can comprise any cross-sectional shape.

Figure 3:
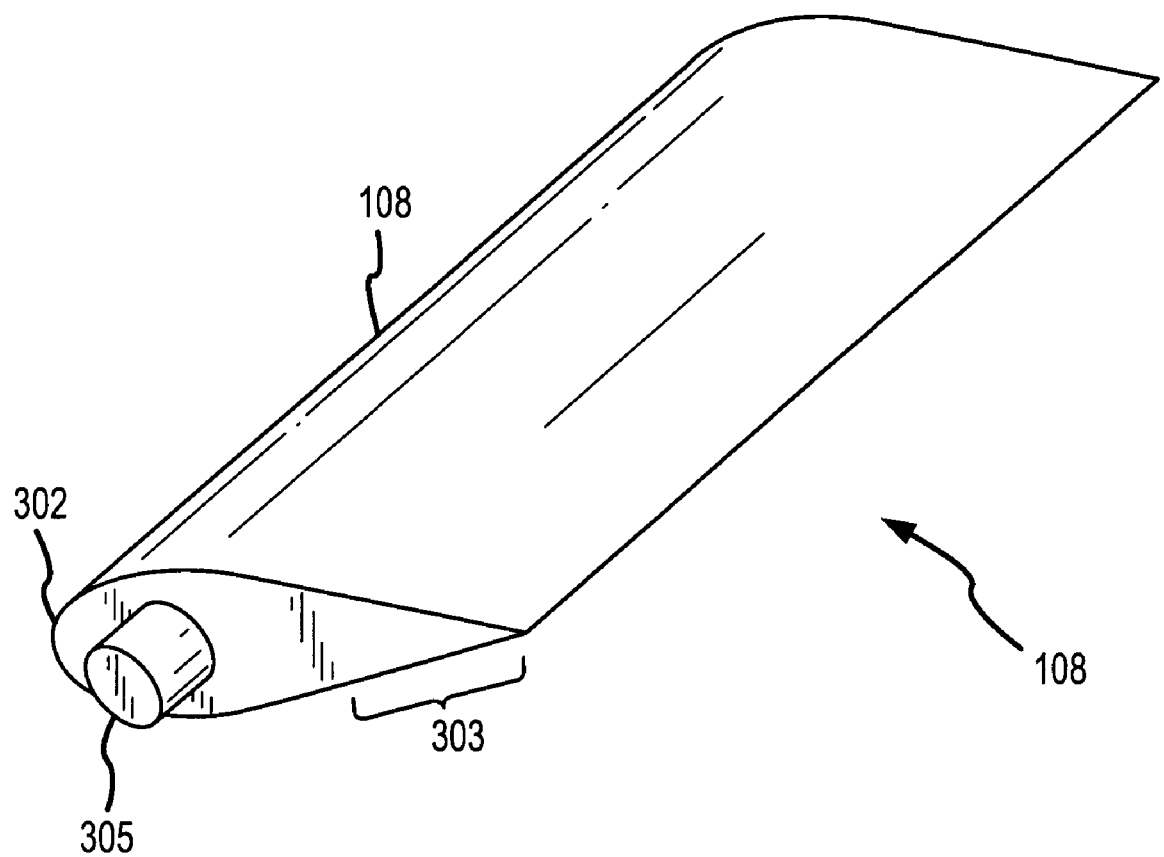
FIG. 3 shows detail of a carbon element according to an embodiment of the invention.

FIG. 3 shows detail of a carbon element 108 according to an embodiment of the invention. In this embodiment, the carbon element 108 features an airfoil-shaped cross-section, including a rounded leading edge 302 and a substantially tapered trailing edge 303. In addition, the carbon element 108 can include end portions 305 that fit into the apertures 106. In one embodiment, the end portions 305 comprise stub axles. The end portions 305 can fit into blind apertures 106 or can extend at least partially through apertures 106 that extend fully through the frame 102. However, it should be understood that the end portions 305 can be included on any shape of carbon element 108.

In one embodiment, the end portions 305 can rotate in the apertures 106 of the frame 102. In another embodiment, the end portions 305 can have a cross-sectional shape that substantially corresponds to a shape of an aperture 106. In this second embodiment, the carbon element 108 is substantially constrained from rotating in the frame 102.

Figure 4:
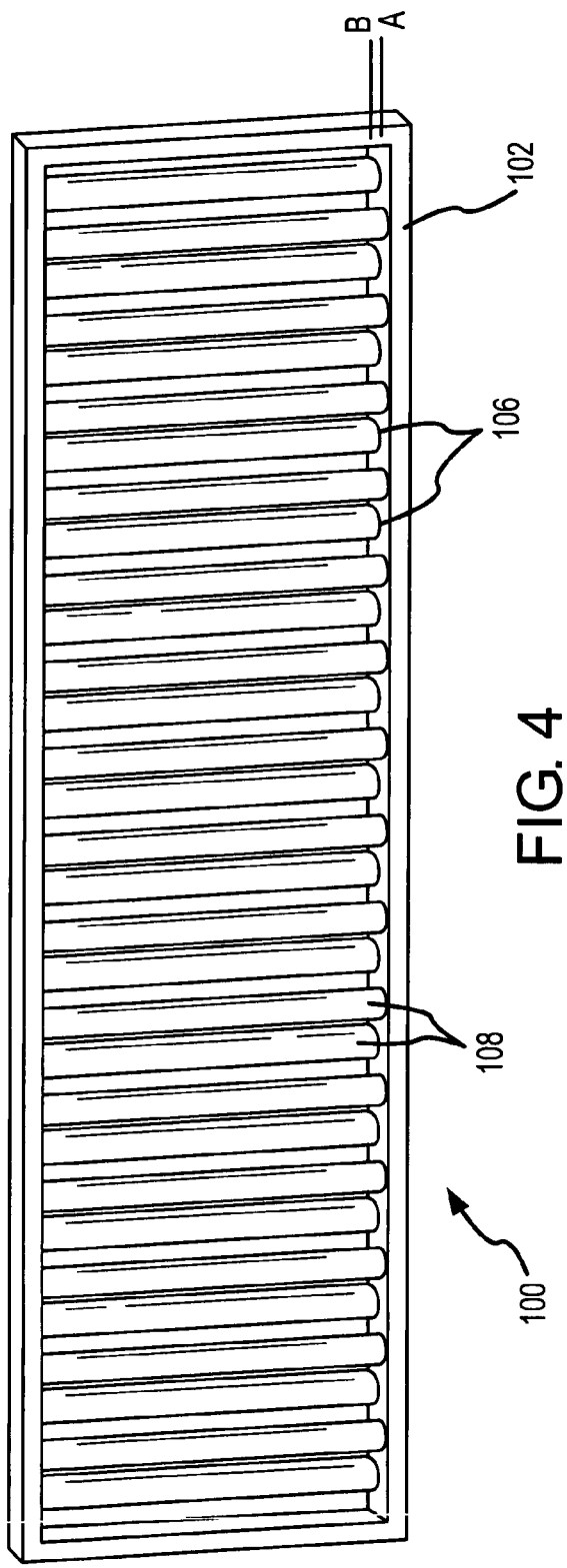
FIG. 4 shows the carbon filter panel according to another embodiment of the invention.

FIG. 4 shows the carbon filter panel 100 according to another embodiment of the invention. In this embodiment, the carbon filter panel 100 includes two rows of carbon elements 108. The two rows of carbon elements 108 are staggered and are aligned substantially along lines A and B. In this manner, the number of carbon elements 108 may be increased. As a result, the amount of contact between the airflow and the carbon elements 108 is increased. The result is an increase in the amount of particles and odors that are absorbed by the carbon filter panel 100.

Figure 5:
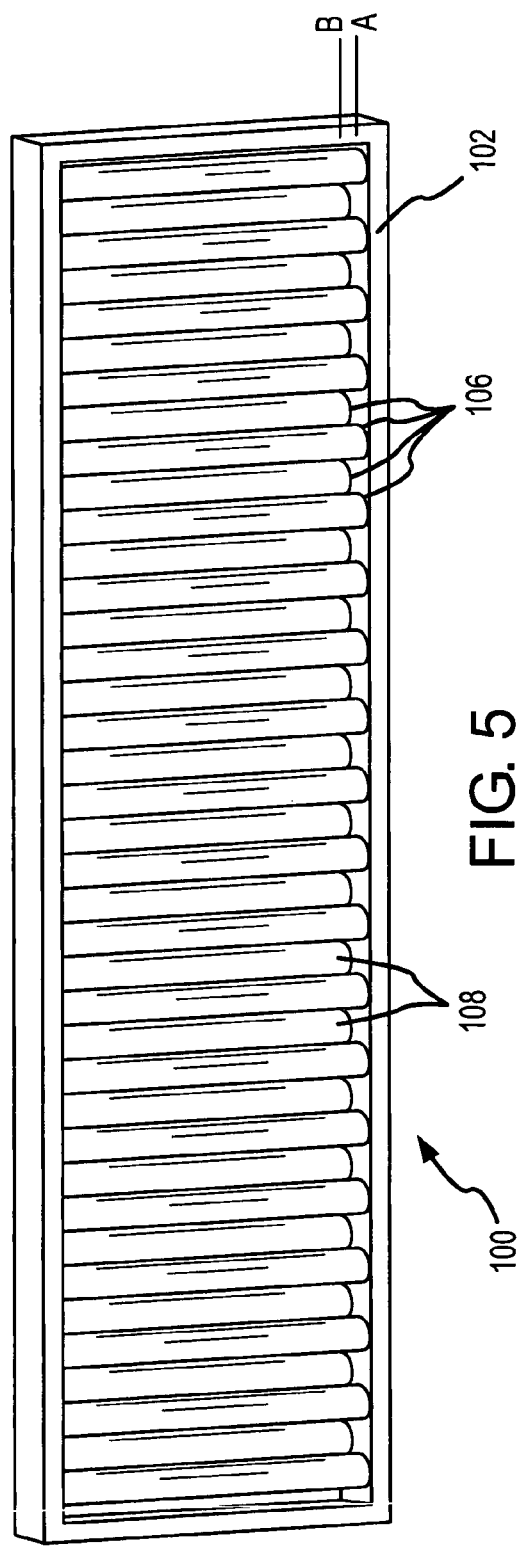
FIG. 5 shows the carbon filter panel according to another embodiment of the invention.
Figure 7:
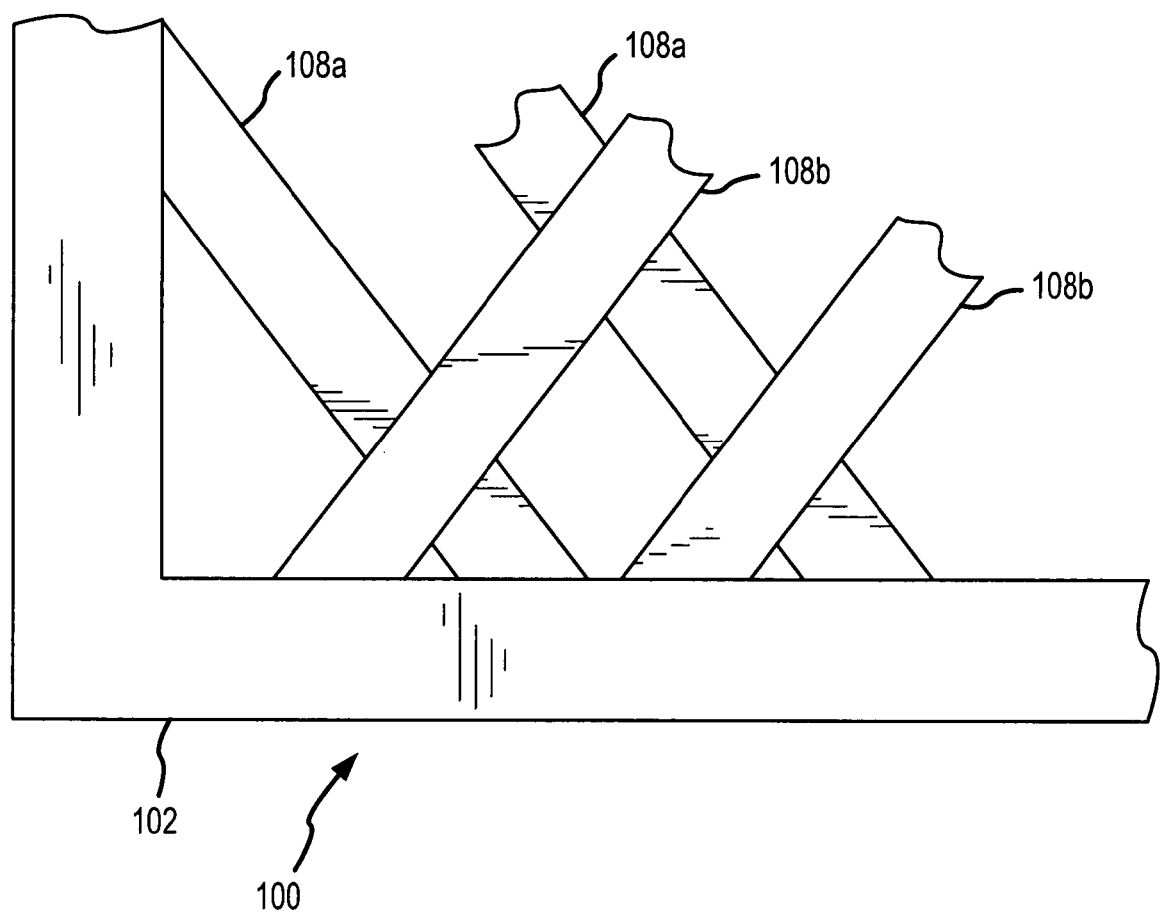
FIG. 7 shows an embodiment that includes a first carbon element row and a second carbon element row.
Figure 8:
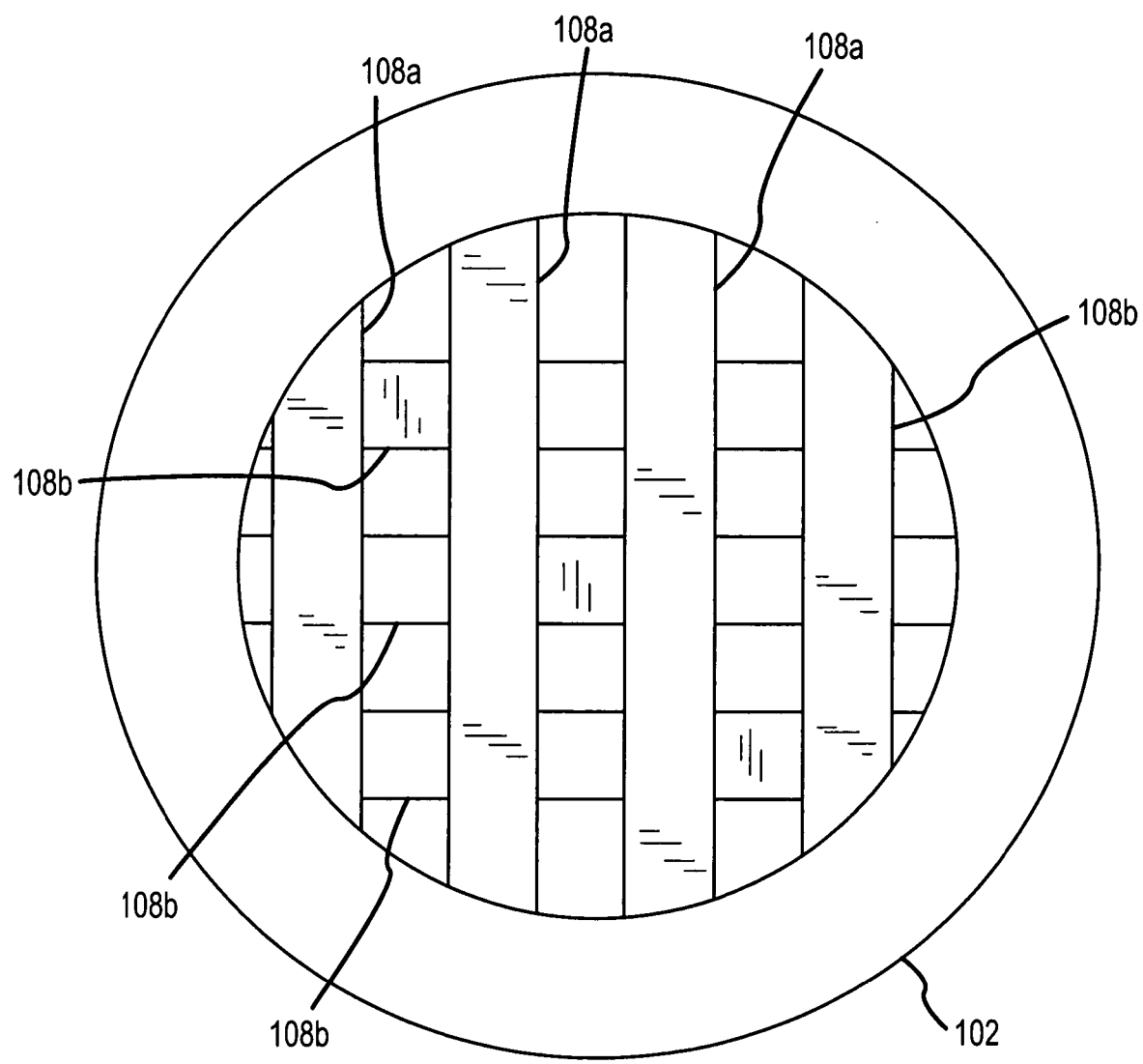
FIG. 8 shows an embodiment that includes a first carbon element row and a second carbon element row.

FIG. 5 shows the carbon filter panel 100 according to another embodiment of the invention. The carbon filter panel 100 in this figure includes more than one row of carbon elements 108, as in FIG. 4. In this embodiment, the spacing between the lines A and B is increased. Consequently, in this embodiment the spacing between carbon elements 108 can be reduced, wherein the airflow achieves a greater level of contact with the carbon elements. In some embodiments, the rows A and B of carbon elements 108 may not overlap. Further, more than two rows of carbon elements 108 can similarly be positioned in the frame 102.

Where the carbon filter panel 100 includes multiple rows, the rows may be formed in different orientations (see FIGS. 7-8). For example, in a two row embodiment, a first row can comprise length-wise elements while a second row can comprise width-wise carbon elements 108. The length-wise and width-wise elements can be non-aligned, i.e., they can be substantially perpendicular or they can be at any desired angle to each other.

Figure 6:
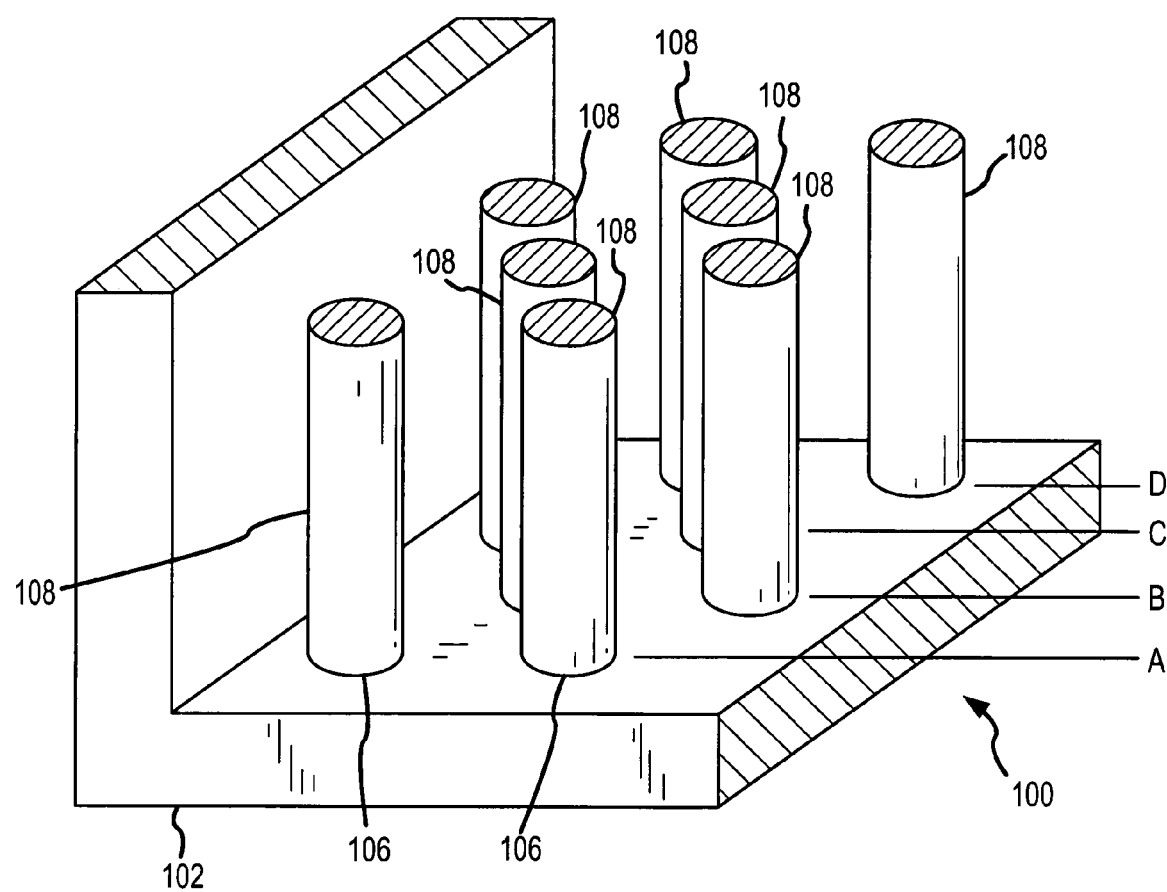
FIG. 6 shows an embodiment of the carbon filter panel wherein four rows A-D of carbon elements are employed.

FIG. 6 shows an embodiment of the carbon filter panel 100 wherein four rows A-D of carbon elements 108 are employed. It can be seen that if the carbon elements 108 are spaced closely enough, the airflow may achieve a serpentine path between and among carbon elements 108. Any number of rows can be employed, and the rows can be partially offset, fully staggered, random, etc.

FIG. 7 shows an embodiment that includes a first carbon element row 108a and a second carbon element row 108b. The first carbon element row 108a is formed at a first orientation and the second carbon element row 108b is formed at a second orientation. In the embodiment shown, the second orientation is at a non-perpendicular angle to the first orientation. However, other orientations can be employed.

FIG. 8 shows an embodiment that includes a first carbon element row 108a and a second carbon element row 108b. The first carbon element row 108a is formed at a first orientation and the second carbon element row 108b is formed at a second orientation. In this embodiment, the second orientation is substantially perpendicular to the first orientation. In addition, this figure shows a substantially circular frame 102, wherein the frame 102 includes only one side member.

One benefit of the invention is that the invention allows airflow characteristics (such as a pressure drop through the filter) to be controlled by choosing the configuration of the carbon filter panel 100. For example, the carbon filter panel 100 can be custom designed for a particular application through choice of the element size, element cross-sectional shape, separation distance S, number of rows, etc. A relatively low pressure drop can be achieved across the carbon filter panel 100 by proper selection of the above characteristics.

Another benefit of the invention is that the separation distance S between individual carbon elements can be varied in a single carbon filter panel 100. For example, the carbon elements 108 in the center of the carbon filter panel 100 can be closer together than the carbon elements 108 at the ends of the carbon filter panel 100. Consequently, more airflow can be forced through (or allowed through) specific regions of the carbon filter panel 100. The carbon filter panel 100 therefore can be designed according to duct restrictions or geometries, desired airflow patterns, etc.

Yet another benefit of the invention is that the carbon elements 108 can be replaceable. For example, in conditions of heavy use, where the carbon elements 108 can become saturated, the individual carbon elements 108 can be removed and replaced by opening the frame 102. As a result, the carbon filter panel 100 can be repairable and/or reconfigurable.

What is claimed is:

1. A carbon filter panel for an air cleaner, comprising:
a frame including one or more side members and a frame interior space; and
a plurality of spaced-apart substantially solid carbon elements extending across the frame interior space, wherein airflow can pass between the plurality of carbon elements and through the carbon filter panel.

2. The carbon filter panel of claim 1, with a carbon element of the plurality of carbon elements comprising an activated carbon element.

3. The carbon filter panel of claim 1, with the plurality of spaced-apart carbon elements comprising a plurality of regularly spaced carbon elements.

4. The carbon filter panel of claim 1, with the carbon filter panel further comprising a plurality of apertures formed in the frame and opening into at least the frame interior space and with a carbon element including end portions that fit into the plurality of apertures.

5. The carbon filter panel of claim 1, with the plurality of carbon elements comprising one row of carbon elements.

6. The carbon filter panel of claim 1, with the carbon filter panel further comprising a plurality of apertures formed in two or more aperture rows in the frame and opening into at least the frame interior space and with the plurality of spaced-apart carbon elements extending across the frame interior space in two or more carbon element rows.

7. The carbon filter panel of claim 1, with the carbon filter panel further comprising a plurality of apertures formed in two or more substantially alternating, spaced-apart aperture rows in the frame and opening into at least the frame interior space and with the plurality of spaced-apart carbon elements extending across the frame interior space in two or more substantially alternating, spaced-apart carbon element rows.

8. The carbon filter panel of claim 1, with the carbon filter panel further comprising a plurality of apertures formed in two or more aperture rows in the frame and opening into at least the frame interior space and with the plurality of spaced-apart carbon elements extending across the frame interior space in two or more non-aligned carbon element rows.

9. A carbon filter panel for an air cleaner, comprising:
a frame including one or more side members and a frame interior space;
a plurality of apertures formed in the frame and opening into at least the frame interior space; and
a plurality of spaced-apart substantially solid carbon elements extending across the frame interior space, with ends of the plurality of carbon elements being received in the plurality of apertures, wherein airflow can pass between the plurality of carbon elements and through the carbon filter panel.

10. The carbon filter panel of claim 9, with a carbon element of the plurality of carbon elements comprising an activated carbon element.

11. The carbon filter panel of claim 9, with the plurality of spaced-apart carbon elements comprising a plurality of regularly spaced carbon elements.

12. The carbon filter panel of claim 9, with a carbon element including end portions that fit into the plurality of apertures.

13. The carbon filter panel of claim 9, with the plurality of carbon elements comprising one row of carbon elements.

14. The carbon filter panel of claim 9, with the plurality of apertures being formed in two or more aperture rows and with the plurality of spaced-apart carbon elements extending across the frame interior space in two or more carbon element rows.

15. The carbon filter panel of claim 9, with the plurality of apertures being formed in two or more substantially alternating, spaced-apart aperture rows and with the plurality of spaced-apart carbon elements extending across the frame interior space in two or more substantially alternating, spaced-apart carbon element rows.

16. The carbon filter panel of claim 9, with the plurality of apertures being formed in two or more aperture rows and with the plurality of spaced-apart carbon elements extending across the frame interior space in two or more non-aligned carbon element rows.

17. A carbon filter panel for an air cleaner, comprising:
a frame including one or more side members and a frame interior space;
a plurality of apertures formed in the frame and opening into at least the frame interior space, with the plurality of apertures being formed in two or more aperture rows; and
a plurality of spaced-apart substantially solid carbon elements extending across the frame interior space in two or more carbon element rows, with ends of the plurality of carbon elements being received in the plurality of apertures, wherein airflow can pass between the plurality of carbon elements and through the carbon filter panel.

18. The carbon filter panel of claim 17, with a carbon element of the plurality of carbon elements comprising an activated carbon element.

19. The carbon filter panel of claim 17, with the plurality of spaced-apart carbon elements comprising a plurality of regularly spaced carbon elements.

20. The carbon filter panel of claim 17, with a carbon element including end portions that fit into the plurality of apertures.

21. The carbon filter panel of claim 17, with the plurality of apertures being formed in two or more substantially alternating, spaced-apart aperture rows and with the plurality of spaced-apart carbon elements extending across the frame interior space in two or more substantially alternating, spaced-apart carbon element rows.

22. The carbon filter panel of claim 17, with the plurality of apertures being formed in two or more aperture rows and with the plurality of spaced-apart carbon elements extending across the frame interior space in two or more non-aligned carbon element rows.

23. A carbon filter panel for an air cleaner, comprising:
a frame including one or more side members and a frame interior space;
a plurality of apertures formed in the frame and opening into at least the frame interior space, with the plurality of apertures being formed in two or more aperture rows; and
a plurality of spaced-apart substantially solid carbon elements extending across the frame interior space in two or more non-aligned carbon element rows, with ends of the plurality of carbon elements being received in the plurality of apertures, wherein airflow can pass between the plurality of carbon elements and through the carbon filter panel.

24. The carbon filter panel of claim 23, with a carbon element of the plurality of carbon elements comprising an activated carbon element.

25. The carbon filter panel of claim 23, with the plurality of spaced-apart carbon elements comprising a plurality of regularly spaced carbon elements.

26. The carbon filter panel of claim 23, with a carbon element including end portions that fit into the plurality of apertures.

* * * * *